United States Patent [19]

Shimp et al.

[11] Patent Number: 5,068,309

[45] Date of Patent: Nov. 26, 1991

[54] LOW TEMPERATURE CURABLE DICYANATE ESTER OF DIHYDRIC PHENOL COMPOSITION

[75] Inventors: David A. Shimp, Prospect; Jeffrey T. Vanderlip, Louisville, both of Ky.

[73] Assignee: Hi-Tek Polymers, Inc., Jeffersontown, Ky.

[21] Appl. No.: 501,231

[22] Filed: Mar. 29, 1990

[51] Int. Cl.$^5$ .............................................. C08G 83/00
[52] U.S. Cl. .................................. 528/211; 528/212; 528/422; 560/301
[58] Field of Search ................... 528/211, 422, 212

[56] References Cited

U.S. PATENT DOCUMENTS 4,839,442 6/1989 Craig .................................. 528/422

Primary Examiner—Harold D. Anderson
Attorney, Agent, or Firm—Herbert P. Price

[57] ABSTRACT

Cyanate esters of 4,4'-[1,3-phenylenebis (1-methylethylidene)] 2,2',6,6'-R-bisphenol when properly catalyzed, can be cured at temperatures in the range of about 250° to about 300° F. to obtain percent cyclotrimerization of the cyanate ester groups of at least 80 percent.

22 Claims, No Drawings

LOW TEMPERATURE CURABLE DICYANATE ESTER OF DIHYDRIC PHENOL COMPOSITION

BACKGROUND OF THE INVENTION

The field of art to which this invention pertains is aryl cyanate esters, i.e., cyanic acid esters of polyhydric phenols.

Cyanate esters are finding increasing use in structural composites, adhesives, and electrical grade insulation. These esters are based on the reaction products of polyhydric phenols and cyanogen halides. Cyanate esters and processes for preparing them are described in a number of patents, examples of which are U.S. Pat. No(s). 3,403,128; 3,755,042; 3,987,230; 4,028,393; 4,330,658; and 4,839,442.

Industry is constantly searching for materials which can be readily processed into products having improved performance properties. There is a need for thermosetting resin compositions which have viscosities of less than 20,000 cps at 25° C. or have crystalline melting points below 100° C. There is also a need for low Tg resin compositions which will cure at temperatures as low as 120° C. to give compositions having low water absorption properties as well as low dielectric loss properties.

Ovens large enough to be used to cure the thermosetting matrices of large composite structures, such as aircraft wings and fuselages, submarine hulls, and antenna reflectors, are not available or practical. Such large structures are generally placed under a tent-like cover and are heated with hot air. The maximum practical temperature which can be obtained under such conditions will range from about 250° F. to about 300° F. (121° C.-149° C.). There is a need for resin systems which will cure in this temperature range.

Composite structures will undergo less outgassing during deployment in the vacuum environment of outer space when the matrix resins absorb less moisture during processing in earth's atmosphere. Microcracking due to thermal cycling imposed when the orbiting space structure passes through the earth's shadow can be reduced or eliminated by incorporating strain-at-break-enhancing thermoplastics into liquid thermosetting resins and/or by reducing residual curing stresses.

Multilayer circuit boards which utilize aramid fibers to match low coefficient of thermal expansion of surface mounted chip packages can similarly benefit in terms of microcrack resistance by employing resins which develop less cure stress or tolerate higher strains.

Absorption of microwave energy by radomes decreases with low dielectric constant (Dk) composite materials. Power loss in antennas is reduced with lower dissipation factor (Df) materials.

Signal propagation delays are reduced in high frequency circuit boards by reducing the Dk of substrate materials. Interconnect materials require a flat Dk response well into the gigahertz frequency range to avoid echo delays caused by mismatched impedance values. Power loss is reduced with decreasing Df values in substrate materials.

SUMMARY OF THE INVENTION

This invention is directed to polycyanate esters of polyhydric phenols. In one aspect, this invention pertains to dicyanate esters of a multi-aromatic ring dihydric phenol. In another aspect, this invention relates to a process for curing the dicyanate esters. In still another aspect, this invention pertains to the cured dicyanate esters.

The dicyanate ester of this invention is 4,4'-[1,3-phenylenebis (1-methylethylidene)]2,2',6,6'-R-bisphenyl cyanate

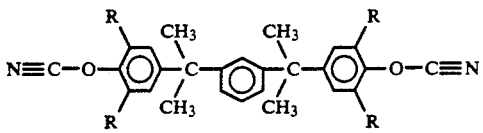

wherein R is independently H or $C_1$ to $C_4$ alkyl. The cyanate ester has a viscosity of about 5000 to about 20,000 cps at 25° C. and a reactivity at 110° C. expressed as % trimerization/hour of less than 0.5. The cyanate ester can be cured by heating at a temperature of about 120° C. to about 150° C. for a time sufficient to obtain at least about 80 percent conversion of the cyanate groups to triazine groups wherein a coordination metal chelate or carboxylate is present, as a catalyst, in the amount of about 20 to about 500 ppm based on the weight of the metal and on the weight of the cyanate ester.

The cured dicyanate ester of this invention has a percent water absorption of no more than about 1 percent, a dielectric constant between about 2.5 and 2.8, and a dissipation factor of about $4 \times 10^{-3}$ to $4 \times 10^{-4}$.

DESCRIPTION OF THE INVENTION

The dicyanate esters of this invention are made by reacting a cyanogen halide with a dihydric phenol in the presence of an acid acceptor. This reaction is well known and is described in U.S. Pat. No(s). 3,755,402 and 4,028,393, which are hereby incorporated by reference. The useful cyanogen halides are cyanogen bromide and cyanogen chloride with the chloride being preferred.

The acid acceptors used to prepare the dicyanate esters are inorganic or organic bases, such as sodium hydroxide, potassium hydroxide, sodium methylate, potassium methylate, and various amines, preferably tertiary amines. Examples of such amines are triethylamine, tripropylamine, diethylpropylamine, pyridine, and the like. A preferred base is triethylamine.

The reaction is conducted in an organic solvent, such as ethylacetate, toluene, xylene, chlorinated hydrocarbons, acetone, diethylketone, methyl isobutyl ketone, etc. Preferred solvents are methylene chloride and methylisobutyl ketone.

The temperature at which the cyanate esterification reaction is conducted will range from about −45° C. to about 0° C., and, preferably, about −35° C. to about −25° C.

The preferred process for preparing the dicyanate esters of this invention is described in U.S. Pat. No. 4,028,393 referred to hereinabove. The process comprises reacting cyanogen chloride in a halocarbon or ketone solvent with a solution of the dihydric phenol and a tertiary amine in a halocarbon or ketone solvent at a temperature below −10° C. for a time sufficient to complete the esterification reaction followed by washing with acidified water, wherein a small excess, based on equivalent weight, of cyanogen chloride is reacted with the dihydric phenol and the amount of tertiary amine is in slightly equivalent excess over the dihydric phenol.

Industry is constantly searching for materials which can be readily processed into products having improved performance properties. There is a need for thermosetting resin compositions which have viscosities of less than 20,000 cps at 25° C. or have crystalline melting points below 100° C. There is also a need for low Tg resin compositions which will cure at temperatures as low as 120° C. to yield compositions having low water absorption properties as well as low dielectric constants and low dissipation factors.

The dihydric phenols from which the dicyanate esters of this invention are made are tri-aromatic ring dihydric phenols having the following structure:

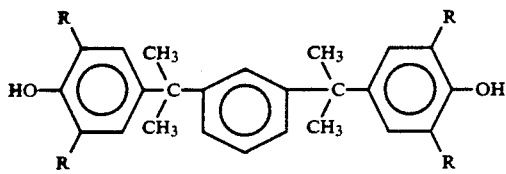

wherein R is independently H or an alkyl group containing 1 to 4 carbon atoms. Preferably R is H. An important feature of this invention is the use of dihydric phenols wherein the substituents on the central aromatic ring are meta to each other. Dicyanate esters made from such dihydric phenols have crystalline melting points below 75° C. and are normally liquid at room temperature, i.e., they exist in a super-cooled liquid state at room temperature. Dicyanate esters derived from triaromatic ring dihydric phenols wherein the substituents on the central ring are para to each other, as disclosed in U.S. Pat. No. 4,157,360, have crystalline melting points well above 100° C. and do not remain in a liquid super-cooled state at room temperature. It is difficult and impractical to use such high melting crystalline materials in their monomeric form in industrial applications since they cannot be melted to pourable liquids in the steam-heated rooms normally used for such procedures. The crystalline monomers must be partially trimerized to form prepolymers which being amorphous are handled more easily in prepreg processing.

The cyanate esters of this invention are normally liquid compositions at room temperature having viscosities of about 5,000 to about 20,000 cps. These esters will sometimes crystallize with age. However, the crystals have low melting points and are readily melted for use in industrial applications, e.g., filament winding, pultrusion, and resin transfer molding. For instance, the dicyanate ester 4,4'-[1,3-phenylenebis(1-methylethylidene)]-bisphenylcyanate, i.e.,

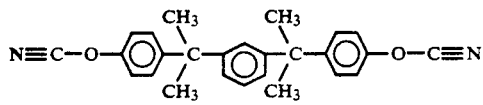

the ester of this invention wherein R is hydrogen, has a melting point of 68° C. In the super-cooled noncrystalline state, the ester has a viscosity of less than 15,000 cps, generally about 7,000 to about 12,000 cps at 25° C.

The dicyanate esters of this invention are stable when stored at room temperature and have a reactivity when measured at 110° C. of less than 0.5 percent trimerization per hour. Reactivity, as used herein, refers to the ability of the uncatalyzed cyanate groups to cyclotrimerize. When such cyclotrimerization occurs, there is a corresponding reduction in cyanate ester content. Cyanate esters, which have high uncatalyzed reactivity, are unstable and cannot be stored for long periods of time without loss of cyanate ester groups, increase in viscosity and eventual gelation.

Cyanate ester content can be determined quantitatively by infrared analysis or by "residual heat of reaction" using a differential scanning calorimeter.

Cyclotrimerization is accompanied by an increase in refractive index which is directly proportional to the conversion of cyanate groups to the triazine ring. A plot of the refractive index versus the percent conversion of cyanate functionality to s-triazine ester, as determined by infrared or differential scanning calorimeter analysis, is linear and the slope constant is readily determined.

The reactivity of cyanate esters can be determined by measuring the change in refractive index at 110° C. and dividing this value by the previously determined slope constant. The esters of this invention have reactivities of less than 0.5 percent trimerization per hour measured at 110° C. Preferably the percent trimerization is less than 0.3 percent.

The curing of polycyanate esters of polyhydric phenols to form crosslinked thermoset resins takes place through the cyclotrimerization of the cyanate ester groups. Useful physical properties are not obtained until at least about 80 percent, preferably 85 percent of the cyanate groups have reacted.

Polycyanate esters of polyhydric phenols are cured to the thermoset state using heat and metal salts and/or active hydrogen containing compounds as catalysts. In order to obtain useful properties from commercially available polycyanate esters, e.g., the dicyanate ester of Bisphenol A, the catalyzed esters must be heated to a temperature of at least 400° F., preferably 450° F. When heated at temperatures below 400° F., even for long periods of time, the trimerization reaction fails to reach the critical 85 percent trimerization needed to obtain useful properties.

The dicyanate esters of this invention can be cured using conventional catalysts and temperatures. However, contrary to the curing procedures for conventional esters, the dicyanate esters of this invention, when properly catalyzed, can be reacted to a useful thermoset state at temperatures as low as 250° F. up to 300° F. When heated within this range of about 250° F. to about 300° F., a percent conversion of cyanate ester groups to cyclotrimerized groups of about 80 to about 85 percent is obtained within 3 hours.

The low temperature curing process is conducted by heating the dicyanate esters of this invention at a temperature of about 250° F. to about 300° F. for a time sufficient to obtain at least about 80 percent cyclotrimerization of the cyanate ester groups using as catalysts a mixture of about 20 ppm to about 500 ppm of a coordination metal chelate or carboxylate wherein said ppm are based on the weight of metal and the weight of cyanate ester, and about 1 to about 10 weight percent, said weight percent being based on the weight of the cyanate ester, of a compound containing an active hydrogen and having a boiling point of at least 160° C. In a preferred process, the amount of metal catalyst is about 50 to about 150 ppm based on the weight of metal and about 2 to about 6 weight percent active hydrogen compound.

The transition metal chelates used as catalysts in this invention are described in U.S. Pat. No. 4,785,075 which is hereby incorporated by reference. The metal carboxylates are described in U.S. U.S. Pat. No(s). 4,604,452 and 4,608,434 which are also incorporated by reference.

Examples of transition metals, i.e., metals having nine or more electrons in the next-to-outermost shell, are copper, manganese, nickel, cobalt, zinc and tin, normally or usually in the divalent state, iron, cobalt and manganese in the trivalent state, and titanium in the tetravalent state. Aluminum, not classed as a transition metal, is also useful when used in chelate form.

The metal chelates useful in this invention are the metal acetylacetonates. The metal carboxylates are the metal salts of carboxylic acids having 4 to about 24 carbon atoms, examples of which are the metal salts of butanoic acid, hexanoic acid, dodecanoic acid, naphthenoic and naphtanoic acid, and fatty acids derived from vegetable oils.

Preferred metal salts are the naphthenates of copper, manganese, nickel, cobalt, and zinc with zinc being preferred. The preferred metal chelate is cobalt acetylactonate.

The active hydrogen containing compounds used as catalysts in this invention are alkyl phenols, monofunctional alcohols and aromatic secondary amines. Useful alkyl phenols are described in U.S. Pat. Nos 4,604,452 and 4,785,075, referred to hereinabove. Useful alcohols are described in U.S. Pat. No. 4,608,434, also referred to hereinabove.

Examples of useful active hydrogen containing compounds are alkyl phenols which contain one or to alkyl substituents, located ortho or para to the phenolic hydroxyl group wherein the total carbon atoms in the alkyl substituents vary from 4 to about 24. A preferred alkylphenol is nonylphenol. Useful alcohols are monohydric alcohols which are liquid at room temperature and which boil above 160° C. at atmospheric pressure, examples of which are dodecanol, benzyl alcohol, monoamyl ether of propylene glcyol, and 5-norbornene2-methanol. Examples of useful amines are N-methyl aniline, alpha-methylbenzyl methylamine, and the like.

The catalysts are preferably used as a solution of the metal salt or chelate in the active hydrogen containing compound, again as described in the afore-mentioned patents.

In carrying out the process of this invention, the solution of metal catalyst and active hydrogen compound is added and mixed with the liquid dicyanate ester at a temperature of about 75° F. to about 212° F. The catalyzed mixture is then deaired and is heated at a temperature of about 200° F. to 250° F. for a time sufficient to obtain gelation with a minimal exothermic temperature increase—no more than about 50° F. Generally, this time will be about 30 to about 120 minutes. The gelled material is then cured by heating at 250° F. to about 300° F. for a time sufficient to obtain at least 80 percent conversion of cyanate ester groups to trimer. In order to obtain full cure, i.e., at least about 95 percent trimerization, additional heating can be conducted at temperatures up to 450° F. using procedures well known to those skilled in the art.

As stated herein, the compositions of this invention can be cured to a conversion of greater than 80 percent (conversion of cyanate ester groups to cyanurate trimer networks) using a maximum cure temperature of 149° C. (300° F.). The resulting cured compositions exhibit exceptional long-term resistance to boiling water (less than about 1.1 weight percent water absorption) and toughness as shown by a strain-at-break of greater than 2.5 percent. Other properties, e.g., flexure strength, flexure modulus, dielectric constant and dissipation factor, are well within useful ranges.

When fully cured, i.e., when heated at temperatures up to about 400° F. (204° C.) or higher to a conversion of at least 95 percent, the compositions have even better long-term water resistance—less than 0.75 weight percent water absorption after 218 hours in boiling water—and an increase in volume of no more than about 0.1 percent after 1000 hours exposure to 25° C. water-vapor at greater than 95 percent relative humidity. The cured compositions exhibit dielectric constants of about 2.5–2.8 and dissipation factors of about $4 \times 10^{-3}$ to $4 \times 10^{-4}$. The Tg of the cured compositions range from about 125°–190° C. and no stress-induced shrinkage occurs during polymerization.

The dicyanate esters of this invention can be blended with polyepoxide resins, thermoplastic resins, bis-maleimide resins, and prepolymers of other cyanate esters to obtain compositions which when cured are useful in numerous industrial applications.

When formulated for particular end uses, additional components can be incorporated in the polycyanate compositions. Such components include reinforcing fibers, colloidal silica flow modifiers, mineral fillers and pigments.

The cured compositions of this invention can be used in vacuum bagged structural composites, transfer molded encapsulates, filmed structural adhesives, printed wiring boards, composites for aircraft primary structures, and the like.

The following examples describe the invention in more detail. Parts and percentages are by weight unless otherwise designated.

EXAMPLE 1

To a suitable reactor were added 1050 parts of methylene chloride. The temperature was lowered to 3° C. and cyanogen chloride was introduced into the reactor as a sparge below the surface of the methylene chloride. 238.4 parts of cyanogen chloride were added over 51 minutes with the temperature rising to 15° C. A solution of 609.7 parts of 4,4'-[1,3-phenylenebis(1-methylethylidene)]bisphenol (Bisphenol M), 360.2 parts of triethyl amine, and 616.7 parts of methylene chloride was added to an addition funnel while cooling the reactor contents to −30° C. When the temperature reached −30° C., the addition of the solution from the funnel was begun. The addition was completed in 35 minutes with the temperature being held at −30° C. After holding at −30° C. for an additional 30 minutes, the temperature was raised to room temperature. The reactor contents were washed with a solution of 10.36 parts of concentrated hydrochloric acid (37%) in 2 liters of water by vigorous stirring for 3 minutes. The stirring was stopped and the top layer was drawn off. The washing step was repeated with a solution of 6.91 parts of concentrated hydrochloric acid in 2 liter of water, followed by washing with 2 liters of deionized water twice. The dicyanate ester product was recovered by distilling off the solvent using a thin film evaporator to a maximum temperature of 80° C. and a vacuum of about 5 mm Hg pressure.

The resulting product, 4,4'-[1,3-phenylenebis(1-methylethylidene)]bisphenylcyanate, was recovered in a yield of 683 parts. The diester had a viscosity at 25° C.

of 11,200 cps, a Gardner color of 2 and a reactivity at 110° C. of less than 0.1 percent per hour.

EXAMPLE 2

For comparison purposes, the dicyanate ester of 4,4'-(p-phenylenediisopropylidene) bisphenol (Bisphenol P) was prepared using substantially the same procedure described in Example 1.

To a suitable reactor were added 893.5 parts of methylene chloride. The temperature was lowered to 0° C. and cyanogen chloride was introduced into the reactor as a sparge below the surface of the methylene chloride. 92.3 parts of cyanogen chloride were added over 36 minutes with the temperature rising to 8° C. A solution was made from 233.55 parts of Bisphenol P, 143.45 parts of triethylamine and 737.5 parts of acetone by heating the mixture to a temperature of 37° C. This solution was then added to the addition funnel fitted on the reactor. The reactor contents were cooled to −30° C., and the funnel contents were added over 53 minutes while keeping the temperatures at −35° C. The reactor contents were then washed with a solution of 16.99 parts of concentrated hydrochloric acid in 1500 parts of water by vigorous stirring for 3 minutes. The stirring was stopped and the top layer was drawn off. The acid washing step was repeated followed by two washes with 2,000 parts of deionized water.

The solution of the cyanate ester product was concentrated from 1060.8 parts to 497 parts using a thin film evaporator. The solution was then held at 4° C. overnight. Dicyanate ester crystals in the amount of 93 parts were recovered. The filtrate was reconcentrated and 126 parts of crystals were recovered. These crystals had a melting point of 126° C.

EXAMPLE 3

Castings were prepared from the dicyanate ester of Bisphenol M (Example 1) as follows: to 160 parts of the dicyanate ester heated to 60° C. was added a solution of 0.25 part of zinc naphthenate in 3.2 parts of nonylphenol. The catalyzed solution was vacuum deaired and poured into preheated mold constructed from silicone treated, 6.3 mm thick aluminum plates spaced 3.2 mm apart with Teflon gaskets. The molds were then heated at 104° C. until the cyanate ester gelled (70 minutes). The cyanate ester was then cured by heating at 149° C. for 3 hours, plus 2 hours at 177° C. and 2 hours at 204° C. The physical properties of the castings were determined after each heating period. The test results are shown in Table 1.

EXAMPLE 4

Casting were also prepared from the dicyanate ester of Bisphenol P (Example 2). An attempt to melt process this dicyanate ester was unsuccessful due to its almost immediate gelation when the catalyst solution was added to the molten ester (126° C.). In order to prepare castings, it was necessary to partially polymerize the monomer to a prepolymer which was amorphous and semi-solid at room temperature. The prepolymer so prepared had a refractive index at 110° C. of 1.5662 which represented a 12 percent conversion of cyanate ester functionality to trimer. The prepolymer was then catalyzed with a solution of zinc naphthenate in nonyl phenol and castings were prepared using the same procedure and temperatures described in Example 3. The time to gel at 104° C. was 2 minutes which is an impractically short time for commercial operations. The physical properties of the castings are listed in Table 1.

TABLE 1

| | Properties of Cured Dicyanate Esters of Bisphenol M and Bisphenol P | | | | | |
|---|---|---|---|---|---|---|
| | Example 1 | | | Example 2 | | |
| Composition, parts | Dicyanate Ester of Bisphenol M (DCBM) | | | Dicyanate Ester of Bisphenol P (DCBP) | | |
| Example 1 | 160 | | | | | |
| Example 2 | | | | 160 | | |
| Nonylphenol | 3.2 | | | 3.2 | | |
| Zinc Naphthenate, 8% Zn | 0.25 | | | 0.25 | | |
| Minutes to Gel at 104° C. | 70 | | | 2 | | |
| Cured State Properties | | | | | | |
| Cure temp °C. | 149 | 177 | 204 | 149 | 177 | 204 |
| % Conversion | 83.5 | 89.3 | 99.1 | 73.9 | 82.3 | 90.1 |
| HDT, °C. | 111 | 131 | 160 | 132 | 149 | 177 |
| Flexure St, ksi | 11.6 | 12.2 | 17.0 | 10.8 | 13.6 | 17.8 |
| Flexure Mod., msi | 0.44 | 0.40 | 0.41 | 0.55 | 0.53 | 0.64 |
| Flexure Strain, % | 2.7 | 3.2 | 4.6 | 2.0 | 2.6 | 3.8 |
| % H$_2$O Abs at 100° C. | | | | | | |
| 24 hours | 0.50 | 0.38 | 0.50 | 0.56 | 0.60 | 0.73 |
| 48 hours | 0.70 | 0.49 | 0.57 | 0.76 | 0.71 | 0.84 |
| 218 hours | 1.07 | 0.67 | 0.71 | 0.94 | 0.83 | 0.92 |
| Specific Gravity | 1.1558 | 1.1555 | 1.1470 | 1.1585 | 1.1518 | 1.1457 |

EXAMPLE 5

Using the same procedure described in Example 3, casting were made from the dicyanate ester of bis (4-hydroxyphenyl)1,1-ethane (dicyanate ester of Bisphenol E) (DCBE) and the dicyanate ester of bis(4-hydroxyphenyl) 2,2-propane (dicyanate ester of Bisphenol A) (DCBA). The physical properties of these castings compared to those of the casting of Example 3 (DCBM) are shown in Table 2.

TABLE 2

| Properties of Cured Dicyanate Esters of Bisphenol A, Bisphenol E and Bisphenol M | | | |
|---|---|---|---|
| | Composition parts | | |
| | DCBM | DCBE | DCBA |
| DCBM | 160 | | |
| DCBE | | 160 | |
| DCBA | | | 160 |
| Nonylphenol | 3.2 | 3.2 | 3.2 |
| Zinc Napthenate | 0.25 | 0.25 | 0.25 |
| Minutes to Gel at | 70 | 100 | 65 |

TABLE 2-continued

Properties of Cured Dicyanate Esters of
Bisphenol A, Bisphenol E and Bisphenol M

| | Composition parts | | |
|---|---|---|---|
| | DCBM | DCBE | DCBA |
| 104° C. Cured State Properties Cure Temp of 149° C. Time 3 hours | | | |
| % Conversion | 83.5 | 75.6 | 73.2 |
| Tg °C. | 128 | 119 | 123 |
| Water ab at 100° C. | | | |
| 24 hours | 0.50 | 1.82 | 1.53 |
| 48 hours | 0.70 | 2.62 | 2.21 |
| 114 hours | 0.92 | 5.51* | 3.48 |
| 218 hours | 1.07 | 9.84* | 5.91* |
| HDT °C. Dry | 111 | 94 | 98 |
| Flexure St, ksi | 11.6 | 9.2 | 0.8 |
| Flexure Mod, msi | 0.44 | 0.43 | 0.38 |
| Flexure Strain % | 2.66 | 2.04 | 0.23 |
| Specific Gravity @ 25° C. | 1.1558 | 1.251 | 1.2247 |
| Dk (1 MHz) | 2.80 | — | — |
| Df (1 MHz) | $1 \times 10^{-3}$ | — | — |
| Additional Cure at 177° C. - 2 hours | | | |
| % Conversion | 89.3 | 83.6 | 74.8 |
| Tg °C. | 149 | 146 | 142 |
| Water Absorption, 100° C. | | | |
| 24 hours | 0.38 | 0.82 | 0.76 |
| 48 hours | 0.49 | 1.18 | 1.15 |
| 114 hours | 0.57 | 1.67 | 1.60 |
| 218 | 0.67 | 2.08 | 2.05 |
| HDT °C. Dry | 131 | 130 | 119 |
| Flexure St., ksi | 12.2 | 11.8 | 5.9 |
| Flexure Mod., msi | 0.40 | 0.48 | 0.42 |
| Flexure Strain, % | 3.15 | 2.52 | 0.46 |
| Specific Gravity @ 25° C. | 1.1555 | 1.2446 | 1.2217 |
| Dk (1 MHz) | 2.70 | 3.05 | — |
| Df (1 MHz) | $4 \times 10^{-4}$ | $6 \times 10^{-3}$ | — |
| Additional Cure at 204° C. - 2 hours | | | |
| % Conversion | 99.1 | 87.5 | 81.8 |
| Tg °C. | 175 | 170 | 173 |
| Water Absorption, 100° C. | | | |
| 24 hours | 0.50 | 0.82 | 0.63 |
| 48 hours | 0.57 | 1.02 | 0.83 |
| 114 hours | 0.64 | 1.33 | 1.09 |
| 218 hours | 0.71 | 1.61 | 1.41 |
| HDT °C. Dry | 160 | 155 | 139 |
| Flexure St., psi | 17.0 | 18.2 | 11.0 |
| Flexure Mod, msi | 0.41 | 0.45 | 0.50 |
| Flexure Strain, % | 4.61 | 4.34 | 2.31 |
| Specific Gravity, @ 25° C. | 1.1470 | 1.2373 | 1.2170 |
| Dk (1 MHz) | 2.64 | 2.99 | 2.98 |
| Df (1 MHz) | $4 \times 10^{-4}$ | $5 \times 10^{-3}$ | $5 \times 10^{-3}$ |

*White, opaque appearance

EXAMPLE 6

Using the same procedure described in Example 3, castings were made from the dicyanate ester of Bisphenol M wherein different amounts of nonyl phenol were used. The casting compositions and the cured state properties are shown in Table 3.

TABLE 3

Properties of Cured Dicyanate Esters of
Bisphenol M Containing Varying Amounts of Nonyl Phenol

| | Composition, parts | | |
|---|---|---|---|
| | A | B | C |
| DCBM | 160 | 160 | 160 |
| Nonyl Phenol | 6.4 | 3.2 | 1.6 |
| Zinc Naphthenate, 8% Zn | 0.25 | 0.25 | 0.25 |
| Min to gel @ 104° C. | 50 | 70 | 80 |
| Cured State Properties Cured Temp °C. of 149° C. Time 3 hours | | | |
| % Conversion | 85 | 83.5 | 83 |
| Water Abs at 100° C. | | | |
| 24 hours | 0.44 | 0.50 | 0.55 |
| 48 hours | 0.60 | 0.70 | 0.82 |
| 114 hours | 0.79 | 0.92 | 1.08 |
| 218 hours | 0.91 | 1.07 | 1.23 |
| HDT °C. Dry | 119 | 111 | 105 |
| Flexure St., ksi | 12.5 | 11.6 | 11.1 |
| Flexure Mod, msi | 0.48 | 0.44 | 0.44 |
| Flexure Strain, % | 2.61 | 2.66 | 2.68 |
| Specific Gravity at 25° C. | 1.1532 | 1.1558 | 1.1601 |
| Additional Cure at 177° C. for 2 hours | | | |
| % Conversion | 92.5 | 89.3 | 86.0 |
| Water Abs at 100° C. | | | |
| 24 hours | 0.42 | 0.38 | 0.36 |
| 48 hours | 0.53 | 0.49 | 0.45 |
| 114 hours | 0.63 | 0.57 | 0.56 |
| 218 hours | 0.70 | 0.67 | 0.66 |
| HDT °C. Dry | 135 | 131 | 123 |
| Flexure St., ksi | 13.4 | 12.2 | 11.0 |
| Flexure Mod, msi | 0.37 | 0.40 | 0.42 |
| Flexure Strain, % | 3.56 | 3.15 | 2.70 |
| Specific Gravity | 1.1504 | 1.1555 | 1.1558 |
| Additional Cure at 204° C. for 2 hours | | | |
| % Conversion | 99.9 | 99.1 | 96 |
| Water Abs at 100° C. | | | |
| 24 hours | 0.47 | 0.50 | 0.46 |
| 48 hours | 0.55 | 0.57 | 0.55 |
| 114 hours | 0.63 | 0.64 | 0.60 |
| 218 hours | 0.66 | 0.71 | 0.66 |
| HDT °C. Dry | 154 | 160 | 162 |
| Flexure St., ksi | 17.0 | 17.0 | 16.9 |
| Flexure Mod, msi | 0.40 | 0.41 | 0.38 |
| Flexure Strain, % | 4.64 | 4.61 | 5.15 |
| Specific Gravity | 1.1426 | 1.1470 | 1.1502 |

EXAMPLE 7

Additional castings were made with the dicyanate ester of bisphenol M which were identical to the castings described in Example 3 except 6 parts nonyl phenol per 100 parts of the cyanate ester (phr) were used. The casting was cured at 121° C. for 3 hours, at 149° C. for 2 additional hours, at 177° C. for 2 additional hours and at 204° C. for 2 additional hours. The percent conversion after each heating period was as follows:

| Temp. | % Conversion |
|---|---|
| 121° C. | 84.8 |
| 149° C. | 93.6 |
| 177° C. | 98.1 |
| 204° C. | 99.9 |

The water absorption for the casting cured at 121° C. was 0.8 percent after 72 hours in boiling water and 1 percent after 250 hours. The water absorption for the casting cured at 177° C. was 0.55 percent after 250 hours.

A casting containing 10 phr nonyl phenol obtained 93.2 percent conversion after 3 hours heating at 149° C.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A heat curable composition comprising the cyanate ester, 4,4'-[1,3-phenylenebis(1-methylethylidene)]-2,2',6,6'-R-bisphenyl cyanate,

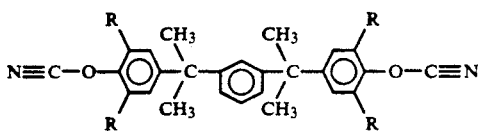

wherein R is independently H or $C_1$ to $C_4$ alkyl, in admixture with about 20 to about 500 weight parts per million based on the weight of metal and of the cyanate ester of a coordination metal chelate or carboxylate and about 1 to about 10 weight percent based on the weight of the cyanate ester of a compound containing an active hydrogen and having a boiling point of at least 160° C.

2. The composition of claim 1 wherein R is H.

3. The composition of claim 1 wherein the coordination metal chelate is cobalt acetylacetonate.

4. The composition of claim 1 wherein the coordination metal carboxylate is zinc naphthenate.

5. The composition of claim 1 wherein the active hydrogen containing compound is an alkyl phenol containing 4 to 24 carbon atoms in the alkyl group.

6. The composition of claim 5 wherein the alkyl phenol is nonyl phenol.

7. The composition of claim 2 wherein the coordination metal carboxylate is zinc naphthenate in the amount of about 50 to about 150 ppm, and the active hydrogen containing compound is nonyl phenol in the amount of about 2 to about 6 weight percent.

8. A process for obtaining a cured composition which comprising heating at a temperature of about 250° F. to about 300° F. for a time sufficient to obtain at least about 80 percent cyclotrimerization of cyanate ester groups the compound 4,4'-[d1,3-phenylenebis (1-methylethylidene)] 2,2',6,6'-R-bisphenyl cyanate

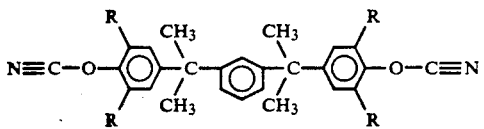

in admixture with about 20 to about 500 weight parts per million based on the weight of metal and of the cyanate ester of coordination metal chelate or carboxylate and about 1 to about 10 weight percent based on the weight of the cyanate ester of a compound containing an active hydrogen and a boiling point of at least 160° C. wherein R is independently H or $C_1$ to $C_4$ alkyl.

9. The process of claim 8 wherein R is H.

10. The process of claim 8 wherein the percent cyclotrimerization is at least about 85 percent.

11. The process of claim 8 wherein the coordination metal chelate is cobalt acetylacetonate.

12. The process of claim 8 wherein the metal carboxylate is zinc napthenate.

13. The process of claim 8 wherein the active hydrogen compound is an alkyl phenol containing 4 to 24 carbon atoms in the alkyl groups.

14. The process of claim 13 wherein the alkyl phenol is nonyl phenol.

15. The process of claim 9 wherein the coordination metal carboxylate is zinc naphthenate in the amount of about 50 to about 150 ppm, the active hydrogen containing compound is nonylphenol in the amount of about 2 to about 6 weight percent and the percent cyclotrimerization is at least 85 percent.

16. The cured composition comprised of cyclotrimerized 4,4'-[1,3-phenylenebis(1-methylethylidene)]-2,2',6,6'-R-bisphenyl cyanate

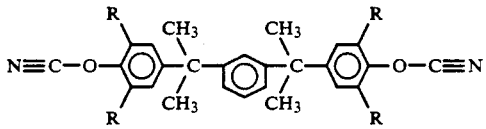

and about 20 to about 500 weight parts per million based on the weight of metal and of the cyanate ester of a coordination metal chelate or carboxylate and about 1 to about 10 weight percent based on the weight of the cyanate ester of a compound containing an active hydrogen and having a boiling point of at least 160° C. wherein R is independently H or $C_1$ to $C_4$ alkyl, wherein the percent cyclotrimerization is at least about 80 percent and wherein the water absorption of the cured casting is no more than about 1 weight percent based on the weight of the casting after 200 hours in boiling water.

17. The composition of claim 16 wherein R is H.

18. The composition of claim 16 wherein the metal chelate is cobalt acetylacetonate.

19. The composition of claim 16 wherein the metal carboxylate is zinc napthenate.

20. The composition of claim 16 wherein the active hydrogen compound is an alkyl phenol containing 4 to 24 carbon atoms in the alkyl group.

21. The composition of claim 20 wherein the alkyl phenol is nonyl phenol.

22. The composition of claim 17 wherein the coordination metal carboxylate is zinc naphthenate in the amount of about 50 to about 150 ppm, the active hydrogen containing compound is nonyl phenol in the amount of about 2 to about 6 weight percent and the percent cyclotrimerization is at least 85 percent.

* * * * *